United States Patent [19]

Sueda et al.

[11] Patent Number: 4,886,803

[45] Date of Patent: Dec. 12, 1989

[54] BENZIMIDAZOLE DERIVATIVES

[75] Inventors: Noriyoshi Sueda, Saitama; Yoshikuni Suzuki, Omiya; Toshiji Sugai, Saitama; Hiroaki Yamada; Makoto Yanai, both of Kawagoe, all of Japan

[73] Assignee: Nisshin Flour Milling Co., Ltd., Japan

[21] Appl. No.: 73,738

[22] Filed: Jul. 15, 1987

[30] Foreign Application Priority Data

Jul. 25, 1986 [JP] Japan ................................ 61-173759
Jul. 10, 1987 [JP] Japan ................................ 62-171139

[51] Int. Cl.⁴ .................... A61K 31/505; C07D 403/14
[52] U.S. Cl. ................................. 514/252; 514/253; 514/269; 514/272; 514/274; 514/275; 514/309; 514/310; 514/312; 514/313; 514/338; 514/359; 514/367; 514/395; 544/238; 544/295; 544/310; 544/317; 544/321; 544/328; 544/331; 544/357; 544/363; 544/364; 544/365; 544/370; 544/495; 546/141; 546/142; 546/143; 546/153; 546/155; 546/157; 546/162; 546/271; 548/159; 548/255; 548/265; 548/268; 548/303
[58] Field of Search ............... 544/295, 238, 310, 317, 544/319, 321, 328, 331, 357, 363, 364, 365, 370, 405; 546/141-143, 153, 155, 157, 162, 271; 548/159, 255, 265, 268, 303; 514/252, 253, 269, 272, 274-275, 309-310, 312-313, 338, 359, 367, 395

[56] References Cited

U.S. PATENT DOCUMENTS 4,634,704  1/1987  Janssens et al. ..................... 544/357

OTHER PUBLICATIONS

Petyunin, et al., (I) "Chemical Abstracts", vol. 97, 1982, Col. 97:92201v.
Petyunin, et al. (II), "Chemical Abstracts," vol. 101, 1984, Col. 101:122559p.
Sueda, et al., "Chemical Abstracts," vol. 108, 1988, Col. 108:167472r.

Primary Examiner—Glennon H. Hollrah
Assistant Examiner—James H. Turnipseed
Attorney, Agent, or Firm—Abelman Frayne Rezac & Schwab

[57] ABSTRACT

Compounds are described of formula (I)

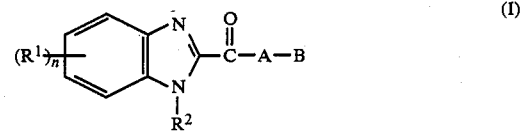

wherein $R^1$ is a hydrogen atom, an alkyl group, an alkoxy group, a dialkylamino group or a halogen atom; n is 1 to 4; $R^2$ is a hydrogen atom, an alkyl group, an unsubstituted or substituted aminoalkyl group, an acyl group, an unsubstituted or substituted aralkyl group, a carboxyalkyl group, an alkoxycarbonylalkyl group or

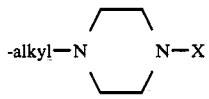

wherein X is an unsubstituted or substituted-phenyl, -benzyl, -benzoyl or -furoyl group; A is $-NR^3-$ where $R^3$ is hydrogen or alkyl, an alkylene or an alkylidene; and B is a heterocyclic group selected from triazolyl, pyridyl, pyridazinyl, pyrimidinyl, pyrazinyl, benzimidazolyl, benzothiazolyl, quinolyl and isoquinolyl, said heterocyclic group being optionally substituted by one or more alkyl, alkoxy, nitro or phenyl group, and the physiologically acceptable acid addition salts thereof. The compound of formula (I) are or cardiotonic activity and thus may be useful for the treatment of circulatory diseases.

14 Claims, No Drawings

BENZIMIDAZOLE DERIVATIVES

BACKGROUND OF THE INVENTION

This invention relates to new benzimidazole derivatives having a cardiotonic effect, to processes for the preparation thereof and to pharmaceutical compositions comprising said derivatives.

Japanese Patent LOP Publn. No. 215388/1986 discloses benzimidazole derivatives having a gastrosecretoinhibitory effect.

Japanese Patent LOP Publn. No. 123115/1987 discloses benzimidazole derivatives having a cytoprotection from gastric acid.

However, the benzimidazole derivatives disclosed above are the compounds wherein the benzimidazole group is attached, through —S—, —SO$_2$— or —S→O, to a pyridyl group or a phenyl group. These compounds are quite different in chemical structure and pharmacological effects from the compounds of the below-mentioned formula (I) according to the present invention wherein the benzimidazole group is attached, through —CO—, to a heterocyclic group.

Further, other benzimidazole derivatives are mentioned in J. Chem. Soc. (C) 25-29 (1967) and Chem. Ber. 105, 337-352 (1972), but these derivatives are different in chemical structure from the compounds of the invention. There is no mention therein of the pharmaceutical use for these derivatives.

DISCLOSURE OF THE INVENTION

According to this invention there are provided new compounds of formula (I) having a cardiotonic effect or physiologically acceptable acid addition salts thereof.

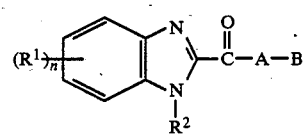

(I)

wherein

R$^1$ is a hydrogen atom, an alkyl group, an alkoxy group, a dialkylamino group or a halogen atom; n is 1 to 4;

R$^2$ is a hydrogen atom, an alkyl group, an unsubstituted or substituted amino-alkyl group, an acyl group, an unsubstituted or substituted aralkyl group, a carboxyalkyl group, an alkoxycarbonylalkyl group or

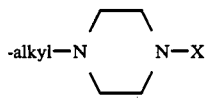

where X is an unsubstituted or substituted-phenyl, -benzyl, -benzoyl or -furoyl group;

A is —NR$^3$— where R$^3$ is hydrogen or alkyl, an alkylene or an alkylidene; and B is a heterocyclic group selected from triazolyl, pyridyl, pyridazinyl, pyrimidinyl, pyrazinyl, benzimidazolyl, benzothiazolyl, quinolyl and isoquinolyl, said heterocyclic group being optionally substituted by one or more alkyl, alkoxy, nitro or phenyl group.

For R$^2$ in the compounds of formula (I), examples of suitable alkyl group include a C$_{1-6}$ preferably C$_{1-4}$ alkyl group, e.g., methyl, ethyl, propyl and butyl; and examples of suitable acyl group include acetyl, propionyl, butyryl and stearoyl. The unsubstituted or substituted amino-alkyl group is for example represented by the formula

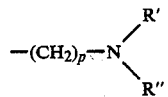

where R' and R'' independently are hydrogen or alkyl and p is 2 to 4, typical examples of said group including aminoethyl, aminopropyl, monomethylaminoethyl, and dimethylaminoethyl. Examples of suitable carboxyalkyl group include carboxymethyl, 3-carboxypropyl and the like. Examples of suitable alkoxycarbonylalkyl groups include methoxycarbonylmethyl, ethoxycarbonylmethyl and the like. Preferred examples of the unsubstituted or substituted aralkyl groups include benzyl and phenetyl. Examples of the group represented by

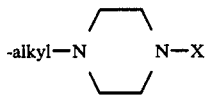

include those of the formula wherein X represents

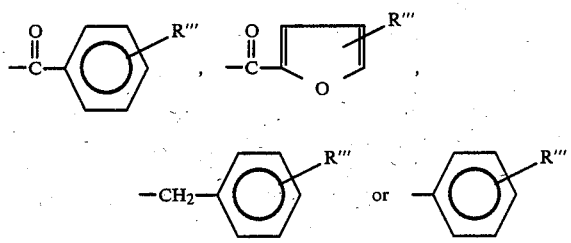

where R''' is hydrogen, alkyl or alkoxy, suitable examples of said groups including (4-dimethoxybenzoyl)-1-piperazinyl)ethyl, (4-furoyl-1-piperazinyl)ethyl, (4-benzyl-1-piperazinyl)ethyl, (4-(methoxyphenyl)-1-piperazinyl)ethyl and (4-(ethoxyphenyl)-1-piperazinyl)ethyl.

For A in the compounds of formula (I), suitable examples of —NR$^3$— includes the unsubstituted or C$_{1-6}$ alkyl-substituted imino such as —NH—, —N(CH$_3$)—, —N(C$_2$H$_5$)—, and examples of suitable alkylene include C$_2$-C$_4$ alkylenes such as methylene, ethylene, propylene and butylene. Further, examples of suitable alkylidene include C$_2$-C$_4$ alkylidenes such as methylene, ethylidene, propylidene, butylidene and the like. Among others, —NH—, —N(CH$_3$)— and methylene are preferred.

Examples of suitable groups for B in the compounds of formula (I) include 5-(1,2,3-triazolyl), 3-(1,2,4-triazolyl), 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-benzimidazolyl, 2-benzothiazolyl, 3-benzoisothiazolyl, 2-quinolyl, 1-isoquinolyl, methyl-substituted pyridyl, methyl-substituted pyrimidyl, methoxy-substituted pyridazinyl and methoxy-substituted benzothiazolyl.

The compounds of formula (I) can be in the form of the acid addition salts made with physiologically acceptable acids, e.g., inorganic acids such as hydrochloric acid and sulfuric acid or organic acids such as fumaric acid, tartaric acid and succinic acid. Thus, it is intended that the reference to the compounds of formula (I) in the present specification is always referred to the acid addition salts.

Typical examples of the present compounds are recited below.

(1) N-(2-Pyridyl)benzimidazole-2-carboxamide
(2) N-(4-Methyl-2-pyrimidinyl)benzimidazole-2-carboxamide
(3) N-(4-Methyl-2-pyridyl)benzimidazole-2-carboxamide
(4) N-(6-Methoxy-2-benzothiazolyl)benzimidazole-2-carboxamide
(5) 1-(β-Dimethylaminoethyl)-N-methyl-N-(2-pyridyl)-benzimidazole-2-carboxamide
(6) (2-Pyridyl)methyl-2-benzimidazolyl ketone
(7) N-(4,6-Dimethyl-2-pyridyl)-5,6-dimethoxybenzimidazole-2-carboxamide
(8) N-(2-Pyridyl)-5-methylbenzimidazole-2-carboxamide
(9) N-Methyl-N-(4,6-dimethyl-2-pyridyl)-1-[2-(4-(3,4-dimethoxybenzoyl)-1-piperazinyl)ethyl]benzimidazole-2-carboxamide
(10) N-(2-Pyridyl)-1-[2-(4-(2-methoxyphenyl)-1-piperazinyl)ethyl]benzimidazole-2-carboxamide
(11) N-(2-Pyridyl)-1-[2-(4-(3,4-dimethoxybenzoyl)-1-piperazinyl)ethyl]-5,6-dimethoxybenzimidazole-2-carboxamide
(12) N-(2-Pyridyl)-1-[2-(4-(3,4-dimethoxybenzoyl)-1-piperazinyl)ethyl]benzimidazole-2-carboxamide
(13) N-Methyl-N-(2-pyridyl)-1-[2-(4-(3,4-dimethoxybenzoyl-1-piperazinyl)ethyl]benzimidazole-2-carboxamide
(14) N-(4,6-Dimethyl-2-pyridyl)-1-carboxymethylbenzimidazole-2-carboxamide
(15) N-(4,6-Dimethyl-2-pyridyl)-1-(β-dimethylaminoethyl-5,6-dimethoxybenzimidazole-2-carboxamide
(16) N-Methyl-N-(4,6-dimethoxy-2-pyridyl)-1-(β-dimethylaminoethyl)benzimidazole-2-carboxamide
(17) N-(4,6-Dimethyl-2-pyridyl)-1-(β-dimethylaminoethyl)benzimidazole-2-carboxamide
(18) N-(5-Methyl-2-pyridyl)-1-(β-dimethylaminoethyl)-benzimidazole-2-carboxamide
(19) N-(2-Pyridyl)-1-methylbenzimidazole-2-carboxamide
(20) N-(2-Pyridyl)-5,6-dimethoxybenzimidazole-2-carboxamide
(21) N-(3-Methyl-2-pyridyl)benzimidazole-2-carboxamide
(22) N-(5-Methyl-2-pyridyl)benzimidazole-2-carboxamide
(23) N-(6-Methyl-2-pyridyl)benzimidazole-2-carboxamide
(24) N-(4,6-Dimethyl-2-pyridyl)benzimidazole-2-carboxamide
(25) N-(4,6-Dimethyl-2-pyridyl)-1-[2-(4-(3,4-dimethoxybenzoyl)-1-piperazinyl)ethyl]benzimidazole-2-carboxamide
(26) N-(4,6-Dimethyl-2-pyridyl)-1-[2-(4-(3,4-dimethoxybenzoyl)-1-piperazinyl)ethyl]-5,6-dimethoxybenzimidazole-2-carboxamide
(27) N-Methyl-N-(4,6-dimethyl-2-pyridyl)-1-[2-(4-(2-furoyl)-1-piperazinyl)ethyl]benzimidazole-2-carboxamide
(28) N-Methyl-N-(4,6-dimethyl-2-pyridyl)-1-[2-(4-benzyl-1-piperazinyl)ethyl]benzimidazole-2-carboxamide
(29) N-Methyl-N-(4,6-dimethyl-2-pyridyl)-1-[2-(4-(2-ethoxyphenyl)-1-piperazinyl)ethyl]benzimidazole-2-carboxamide
(30) N-(4-Methyl-2-pyridyl)-1-[2-(4-(2-methoxyphenyl)-1-piperazinyl)ethyl]benzimidazole-2-carboxamide
(31) N-(4,6-Dimethyl-2-pyridyl)-1-[2-(4-(2-methoxyphenyl)-1-piperazinyl)ethyl]benzimidazole-2-carboxamide
(32) N-Methyl-N-(4,6-dimethyl-2-pyridyl)-1-benzylbenzimidazole-2-carboxamide
(33) N-(4,6-Dimethyl-2-pyridyl)-1-benzylbenzimidazole-2-carboxamide
(34) N-(4,6-Dimethyl-2-pyridyl)-1-phenethylbenzimidazole-2-carboxamide
(35) N-(4,6-Dimethyl-2-pyridyl)-1-(3,4-dimethoxyphenethyl)benzimidazole-2-carboxamide
(36) N-(4-Phenyl-2-pyridyl)benzimidazole-2-carboxamide
(37) N-(5-Nitro-2-pyridyl)benzimidazole-2-carboxamide
(38) N-Methyl-N-(4,6-dimethyl-2-pyridyl)benzimidazole-2-carboxamide
(39) N-(2-Pyridyl)-1-(ethoxycarbonylmethyl)benzimidazole-2-carboxamide
(40) N-(4,6-Dimethyl-2-pyridyl)-1-(ethoxycarbonylmethyl)benzimidazole-2-carboxamide
(41) N-(4-Phenyl-2-pyridyl)-1-(ethoxycarbonylmethyl)-benzimidazole-2-carboxamide
(42) N-(3-Pyridyl)benzimidazole-2-carboxamide
(43) N-(4-Pyridyl)benzimidazole-2-carboxamide
(44) N-(2-Pyrazinyl)benzimidazole-2-carboxamide
(45) N-(2-Pyrimidinyl)benzimidazole-2-carboxamide
(46) N-(3-(1,2,4-triazolyl)benzimidazole-2-carboxamide
(47) N-(2-Quinolyl)benzimidazole-2-carboxamide
(48) N-(1-Isoquinolyl)benzimidazole-2-carboxamide
(49) N-(4-pyridyl)-5,6-dimethoxybenzimidazole-2-carboxamide
(50) N-(6-methoxy-3-pyridazinyl)-5,6-dimethoxybenzimidazole-2-carboxamide
(51) 2-[(2-benzimidazolyl)acetyl]benzimidazole This invention also relates to processes for the preparation of the compounds having formula (I). The processes comprise the following (a) and (b).

(a) A compound of formula (II)

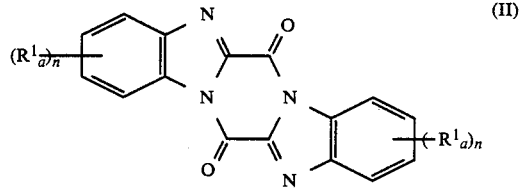

wherein $R^1_a$ is a hydrogen atom, an alkyl group, or a halogen atom and n is 1 to 4, is reacted with a compound of formula (III)

$$Z—A—B \qquad (III)$$

wherein A and B are as defined above and Z is a hydrogen atom, lithium, sodium or potassium, to form a compound of formula (I'$_a$)

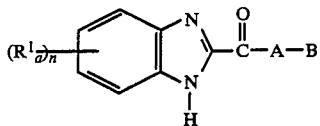

wherein A, B, R¹$_a$ and n are as defined above, or
(b) A compound of formula (IV)

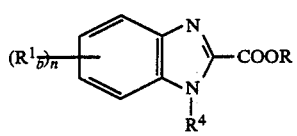

wherein R¹$_b$ is a hydrogen atom, an alkyl group, an alkoxy group or a dialkylamino group, R is an alkyl group, n is as defined above, and R⁴ is a protective group, is reacted with a compound of formula (III')

 (III')

wherein A is as defined above, B' is a heterocyclic group selected from pyridyl, pyridazinyl, pyrimidinyl, pyrazinyl, benzothiazolyl, quinolyl and isoquinolyl, said heterocyclic group being optionally substituted by one or more alkyl, alkoxy, nitro or phenyl group, and Z' is lithium, sodium, potassium or dialkylaluminum, and then the protective group is removed to form a compound of formula (I'$_b$)

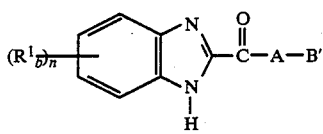

wherein A, B', R¹$_b$ and n are as defined above, and optionally the compounds of formulae (I'$_a$) and (I'$_b$) are treated with an alkylating agent or an acylating agent to convert to the compounds of formula (I) wherein R² is the substituents other than hydrogen, or if desired the compounds thus obtained are converted to the physiologically acceptable acid addition salts according to conventional methods.

According to the process (a), the reaction between compounds of formula (II) and those of formula (III) is carried out in a polar aprotic solvent, preferably dimethyl sulfoxide (DMSO) or hexamethylphosphoric triamide (HMPT), and ordinarily at a temperature between 10° C. and 100° C. or more. A molar ratio of the compounds (II) to the compounds (III) is generally about 1:2. Preferably, the compounds (III) are used in slight excess.

Compounds of formula (II) may be prepared by processes known from any literature, e.g., JACS 65, 1072 (1943).

Most of the compounds of formula (III) are commercially available and other compounds can be prepared by processes known from any literatures, e.g., J. Org. Chem. 48, 2933 (1983); Org. Reactions, 1, 91; and JACS 80, 980 (1958).

The alkyl-substituted 2-(methylamino)pyridines can be prepared by formylation of the corresponding alkyl-substituted 2-aminopyridines in an ordinary manner followed by reduction with lithium aluminum hydride.

Purification of the compounds (I) obtained by the process (a) is carried out by known processes, e.g., recrystallization from a solvent such as a mixed solution of chloroform/methanol, column chromatography on silica gel and the like.

The process (b) is illustrated by the following scheme.

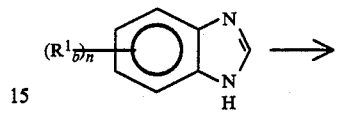

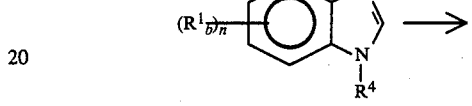

(X)

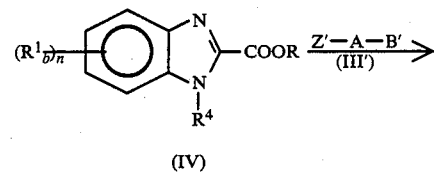

(IV)

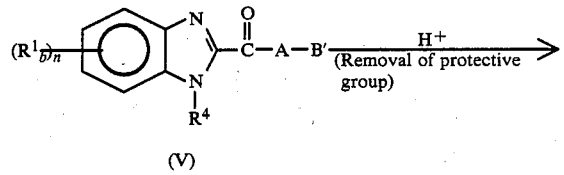

(V)

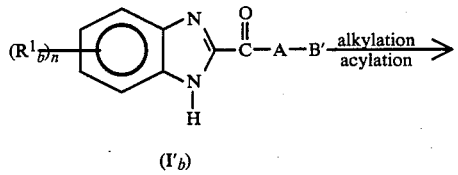

(I'$_b$)

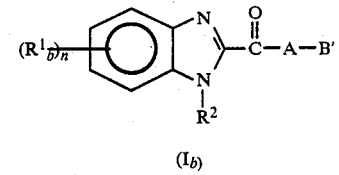

(I$_b$)

wherein R, R¹$_b$, R², R⁴, n, A and B' are as defined above.

Compounds of formula (X) can be synthesized by reacting benzimidazoles with appropriate halides in the presence of a base. In case of using said halides, e.g., methoxymethyl chloride, ethoxymethyl chloride, methoxymethyl bromide or ethoxymethyl bromide, polar aprotic solvents such as DMSO are preferably used as a solvent for reaction. The base used includes alkali metal hydroxides, e.g., sodium hydroxide, potassium hydroxide and alkali metal hydrides, e.g., sodium hydride, potassium hydride or the like. In case of using as halides N,N-dialkylsulfamoyl halides, e.g., N,N-dimethylsulfamoyl chloride or N,N-dimethylsulfamoyl bromide, the solvents for reaction are preferably inert solvents such as dichloromethane, chloroform and toluene. The base used includes tertiary amines, e.g., triethylamine, tri-n-propylamine and the like. Pyridine, quinoline and picoline can be used for both the reaction solvent and the base.

Compounds of formula (IV) can be synthesized by reacting the compounds (X) dissolved in a solvent such as ether, tetrahydrofuran with an alkyl lithium, e.g., n-butyl lithium followed by reaction with a lower alkyl ester of chloroformic acid.

Subsequently, compounds of formula (IV) are reacted with compounds of formula (III') (for example, Z=Na) to prepare compounds of formula (V). The reaction is preferably carried out in a polar aprotic solvent, preferably DMSO or HMPT. In general, the reaction is carried out at a temperature between 10° and 100° C., preferably at room temperature. Generally, a molar ratio of the compounds (IV) to the compounds (III') ranges from 1:1 to 1:2. Preferably, the compounds (III') are used in slight excess.

Compounds of formula (V) are prepared by reacting compounds of formula (IV) with compounds of formula (III') (for example, Z'=dimethylaluminum) in a solvent, e.g., dichloromethane or benzene, at a temperature between 10° C. and a reflux temperature, preferably at room temperature. A molar ratio of the compounds (IV) to the compounds (III') is preferably from 1:1 to 1:2.

The compounds of formula (V) thus prepared can be purified by known processes, e.g., column chromatography on silica gel and the like. Subsequently, compounds of formula (V) are subjected to acid hydrolysis according to an ordinary method to remove the protective group ($R^4$), thus obtaining compounds of formula ($I'_b$). Examples of the protective groups $R^4$ include N,N-dimethylsulfamoyl, methoxymethyl, ethoxyethyl or the like.

Alternatively, suitable $R^2$ substituents in formula (I) can be introduced by direct alkylation or acylation of compounds wherein $R^2$ is hydrogen, e.g., compounds of formula ($I'_a$) or ($I'_b$) according to the processes of the invention. These reactions are conducted under usual conditions using known alkylating or acylating agents. The alkylation will proceed smoothly in a polar aprotic solvent such as DMSO or the like in the presence of a base such as sodium hydride, potassium hydride or the like. The acylation are conveniently conducted in an inert solvent such as chloroform, THF or the like in the presence of a tertiary amine such as triethylamine, pyridine or the like.

Examples of the alkylating and acylating agents used include alkyl halides such as methyl iodide, ethyl chloride; aminoalkyl halides such as aminoethyl chloride, aminopropyl chloride, dimethylaminoethyl chloride; aralkyl halides such as benzyl chloride, phenethyl chloride; acid anhydrides such as acetic anhydride, propionic anhydride; acid halides such as acetyl chloride, benzoyl chloride; alkoxycarbonyl alkyl halide; (4-substituted-1-piperazinyl)alkyl halide represented by the formula

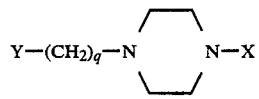

wherein X is as defined for the formula (I), Y is a halogen atom and q is 2-4, e.g. (4-(dimethoxybenzoyl)-1-piperazinyl)ethyl halide, (4-furoyl-1-piperazinyl)ethyl halide, (4-benzyl-1-piperazinyl)ethyl halide, (4-(methoxyphenyl)-1-piperazinyl)ethyl halide and (4-(ethoxyphenyl)-1-piperazinyl)ethyl halide.

Physiologically acceptable acid addition salts of the compounds of formula (I) according to the present invention may be prepared by the application or adaptation of known methods for the preparation of salts of organic bases, for example, by reacting the compounds of the formula (I) with the appropriate acid in a suitable solvent. Examples of addition salts include the salts of inorganic acids such as hydrochloride, sulfate, phosphate, and the salts of organic acids such as fumarate, tartrate, citrate, acetate, propionate, and butyrate.

The compounds of formula (I) are of prominent cardiotonic activity causing a selective increase in the myocardial contractility without increase in heart rate, and these compounds can be used for the treatment and prevention of circulatory diseases which include heart failure, arrhythmia, angina pectoris, hypertension and the like.

Thus, the present invention also relates to pharmaceutical compositions which comprises as an active ingredient the compounds of formula (I) and/or physiologically acceptable acid addition salts thereof used for the treatment and prevention of the above-mentioned diseases.

The pharmaceutical compositions of the invention are formulated by the methods well known by those skilled in the art.

In general, the pharmaceutical compositions of the invention can be administered orally or parenterally in pharmacological dosage forms, such as tablets, capsules, suppositories, troches, syrups, granules, powders, suspensions, injections and the like. The tablets can be molded in the double- or multi-layer together with other agents. Further, the tablets can be coated, if necessary, with conventional coating materials, e.g., sugar coated, film coated or enteric coated.

The additives used for solid preparations include for example lactose, white sugar, crystalline cellulose, cornstarch, calcium phosphate, sorbitol, glycine, carboxymethyl cellulose, gum arabic, polyvinyl pyrrolidone, hydroxypropyl cellulose, glycerin, polyethylene glycol, stearic acid, magnesium stearate, talc and the like.

For semi-solid preparations are used vegitable or synthetic waxes or fats.

The additives used for liquid preparations include for example sodium chloride, sorbitol, glycerin, olive oil, almond oil, propylene glycol, ethyl alcohol and the like.

In these pharmaceutical compositions the active ingredient is ordinally contained in an amount of 0.1 to 100% by weight based on the total weight of the composition. For oral preparations the active ingredient will be in the range of 1 to 50% by weight and for injectable preparations it will be in the range of 0.1 to 10% by weight.

A daily dosage of active ingredient of the invention is in the range of 1 to 1000 mg, which may conveniently be administered in one or more doses.

The precise dose employed will vary depending on the age, sex and condition of the patient as well as the route of administration.

To further illustrate this invention, and not by way of limitation, the following examples are given. Parts are by weight and temperatures are in centigrade unless otherwise specified.

SYNTHESIS OF INTERMEDIATE

Intermediate 1

1-(N,N-Dimethylsulfamoyl)-5,6-dimethoxybenzimidazole

A suspension of 5,6-dimethoxybenzimidazole (6.2 g) in dichloroethane (100 ml) was added to N,N-dimethylsulfamoyl chloride (5.3 g) and triethylamine (6 g) was added dropwise while stirring. After the mixture was reacted at room temperature for 24 hours, the reaction solution was washed with an aqueous sodium hydrogen carbonate solution and then with a saturated saline solution and dried over anhydrous $Na_2SO_4$. The solvent was distilled off, precipitated crystals were filtered, washed with n-hexane and dried to give the title compound (8.57 g).

M.P. 139.0° C.

IR (nujol): 1500, 1215, 1140, 1030, 720 $(cm^{-1})$ $^1$H-NMR ($CDCl_3$, TMS): 2.90 (s, 6H), 3.95 (s, 6H), 7.28 (s, 1H), 7.33 (s, 1H), 8.10 (s, 1H).

Intermediate 2

1-(N,N-Dimethylsulfamoyl)-2-ethoxycarbonyl-5,6-dimethoxybenzimidazole 1-(N,N-dimethylsulfamoyl)-5,6-dimethoxybenzimidazole (5.70 g) was dissolved in dry THF (170 ml) in a dry argon atmosphere, cooled to −60° C. and a solution of n-butyl lithium (1.58M) in hexane (15.2 ml) was added dropwise and stirred for 30 minutes. After ethyl chloroformate (2.60 g) was added dropwise, the mixture was slowly returned to room temperature and allowed to react overnight. THF was distilled off, the residue was dissolved in ethyl acetate, washed with water and dried over anhydrous $Na_2SO_4$, and the solvent was distilled off. Purification of the residue by column chromatography on silica gel gave the title compound (5.13 g) as an oily product.

$^1$H-NMR ($CDCl_3$, TMS): 1.46 (t, 3H), 3.08 (s, 6H), 3.95 (s, 3H), 3.99 (s, 3H), 4.48 (q, 2H), 7.24 (s, 1H), 7.39 (s, 1H)

Intermediate 3

1-Ethoxymethyl-2-ethoxycarbonylbenzimidazole

1-Ethoxymethylbenzimidazole (1.76 g) was dissolved in dry THF (40 ml) in a dry argon atmosphere, cooled to −60° C., and a solution of n-butyl lithium (1.58M) in hexane (9 ml) was added dropwise with stirring and allowed to react for 1 hr. After ethyl chloroformate (1.62 g) was added dropwise, the mixture was slowly returned to room temperature and allowed to react overnight. THF was distilled off, the residue was dissolved in ethyl acetate, washed with water, dried over anhydrous $Na_2SO_4$, and the solvent was distilled off. Purification of the residue by column chromatography on silica gel gave the title compound (0.89 g) as an oily product.

$^1$H-NMR ($CDCl_3$, TMS): 1.18 (t, 3H), 1.31 (t, 3H), 3.50 (q, 2H), 4.24 (q, 2H), 5.61 (s, 2H), 7.35 (m, 2H), 7.60 (m, 1H), 7.85 (m, 1H).

EXAMPLE 1

N-(2-Pyridyl)benzimidazole-2-carboxamide

In a dry argon atmosphere, 2-aminopyridine (4.0 g) was dissolved in dry dimethylsulfoxide (DMSO) (100 ml), 60% sodium hydride (1.7 g) was added and stirred at room temperature for 1 hr. Dibenzimidazo-(1,2-a,1′,2′-d)-tetrahydropyrazine-6,12-dione (5.0 g) was added in portions under ice-cooling and reacted at room temperature for 2 hrs. After the reaction was complete, the mixture was diluted with a mixed solution of chloroform/methanol (9:1), washed twice with a saturated saline solution, dried over anhydrous $Na_2SO_4$, and the solvent was distilled off. Recrystallization of the residue from a mixed solution of chloroform/methanol/isopropyl ether gave the title compound (4.37 g).

M.P. 206.3° C.

IR (KBr): 3250, 1660, 1580, 1540, 1440, 1320, 735 $(cm^{-1})$ $^1$H-NMR (DMSO-$d_6$, TMS): 7.22 (dd, 1H), 7.35 (m, 2H), 7.70 (m, 2H), 7.92 (dt, 1H), 8.21 (d, 1H), 8.42 (d, 1H), 10.14 (bs, 1H), 13.65 (bs, 1H)

Subsequently, N-(2-pyridyl)benzimidazole-2-carboxamide (1.0 g) was dissolved in a mixed solution of chloroform/ethanol (1:1) (50 ml) and 1N hydrogen chloridethanol solution (4.2 ml) was added. The solvent was distilled off under reduced pressure, and the precipitated crystals were filtered and dried to give the hydrochloride of the title compound (0.90 g).

M.P. 209.2° C.

IR (KBr): 3420–3140, 1715, 1650, 1580, 1540, 1450, 1300, 1220, 760 $(cm^{-1})$ $^1$H-NMR (DMSO-$d_6$, TMS): 7.40 (m, 3H), 7.75 (m, 2H), 8.11 (dt, 1H), 8.22 (d, 1H), 8.49 (d, 1H).

EXAMPLE 2

N-(4-Methyl-2-pyrimidinyl)benzimidazole-2-carboxamide

In a dry argon atmosphere, 2-amino-4-methylpyrimidine (4.0 g) was dissolved in dry DMSO (50 ml), sodium hydride (1.5 g) was added and stirred at room temperature for 1 hr. Dibenzimidazo-(1,2-a,1′,2′-d)tetrahydropyrazine-6,12-dione (5.0 g) was added in portions under ice-cooling and reacted at room temperature for 2 hrs. After the reaction was complete, the reaction solution was poured into ice-cold water saturated with ammonium chloride, and precipitated crystals were obtained by filtration. Re-crystallization of the crystals from a mixed solution of chloroform/methanol/isopropyl ether gave the title compound (3.10 g).

M.P. 264.5° C.

IR (nujol): 3360, 3200, 1710, 1595, 1310, 750 $(cm^{-1})$ $^1$H-NMR (DMSO-$d_6$+$CD_3OD$, 9:1, TMS); 2.25 (s, 3H), 7.20 (m, 1H), 7.34 (m, 2H), 7.62 (m, 1H), 7.82 (m, 1H), 8.64 (m, 1H)

EXAMPLE 3

N-(4-Methyl-2-pyridyl)benzimidazole-2-carboxamide

A mixture of 2-amino-4-methylpyridine (1.25 g) and dibenzimidazo-(1,2-a,1′,2′-d)tetrahydropyrazine-6,12-dione (1.50 g) was reacted at 100° C. for 5 hrs in dry DMSO (30 ml) in a dry argon atmosphere. After completion of the reaction, the reaction solution was treated in the same way as mentioned in Example 1 to give the title compound (1.26 g)
M.P. 262.2° C.
IR (nujol): 3360, 3250, 1670, 1545, 730 (cm$^{-1}$)
$^1$H-NMR (CDCl$_3$+CD$_3$OD 9:1, TMS): 2.43 (s, 3H), 6.99 (d, 1H), 7.3–8.0 (4H), 8.13 (s, 1H), 8.22 (d, 1H)

EXAMPLE 4

N-(6-Methoxy-2-benzothiazolyl)benzimidazole-2-carboxamide

2-Amino-6-methoxybenzothiazole (5.3 g) and dibenzimidazo-(1,2-a,1',2'-d)-tetrahydropyrazine-6,12-dione (4.0 g) were reacted and treated in the same manner as mentioned in Example 2 to give the title compound (4.95 g).
M.P. 245.5° C.
IR (nujol): 3300, 3200, 1690, 1605, 1470, 1220, 750 (cm$^{-1}$)
$^1$H-NMR (CDCl$_3$, TMS): 1.55 (bs, 2H), 3.95 (s, 3H), 7.09 (dd, 1H), 7.3–7.9 (6H)

EXAMPLE 5

N-Methyl-N-(2-pyridyl)benzimidazole-2-carboxamide

In a dry argon atmosphere, 2-(methylamino)pyridine (4.0 g) was dissolved in dry DMSO (50 ml), sodium hydride (1.5 g) was added and stirred at room temperature for 1 hr. Dibenzimidazo-(1,2-a,1',2'-d)tetrahydropyrazine-6,12-dione (5.0 g) was added slowly under ice-cooling, stirred for 1 hr and allowed to stand overnight. The reaction solution was poured into aqueous saturated ammonium chloride solution, formed crystals were filtered, washed with water and recrystallized from a mixed solution of chloroform/methanole to give the title compound (6.20 g).
IR (nujol): 3050, 1640, 1590, 1435, 1340, 730 (cm$^{-1}$)
$^1$H-NMR (CDCl$_3$+DMSO-d$_6$, TMS): 3.64 (s, 3H), 7.1–7.55 (6H), 7.78 (t, 1H), 8.32 (d, 1H)

EXAMPLE 6

1-(β-Dimethylaminoethyl)-N-methyl-N-(2-pyridyl)benzimidazole-2-carboxamide

N-Methyl-N-(2-pyridyl)benzimidazole-2-carboxamide (1.0 g) prepared in Example 5 was dissolved in dry DMSO (20 ml), 60% sodium hydride (0.17 g) was added and stirred at room temperature for 1 hr in an argon atmosphere. Excess β-dimethylaminoethyl chloride was added to the mixture and reacted at room temperature under agitation for 20 hrs. The reaction solution was diluted with chloroform, washed with water, dried over anhydrous Na$_2$SO$_4$ and the solvent was distilled off. Purification of the residue by column chromatography on silica gel (using silica gel manufactured by Merck Co., Ltd.) gave the title compound (0.88 g) as an oily product.
IR (neat): 1650, 1595, 1350, 1040, 740 (cm$^{-1}$)
$^1$H-NMR (CDCl$_3$, TMS): 2.27 (s, 6H), 2.72 (t, 2H), 3.67 (s, 3H), 4.56 (t, 2H), 7.05 (dd, 1H), 7.15–7.65 (6H), 8.33 (d, 1H)

EXAMPLE 7

(2-Pyridyl)methyl-2-benzimidazolyl ketone

2-Methylpyridine (3.9 g) was dissolved in dry THF (70 ml), 15% n-butyl lithium (27 ml) was added dropwise while ice-cooling in an argon atmosphere and stirred at room temperature for 30 minutes. Dibenzimidazo-(1,2-a,1',2'-d)-tetrahydropyrazine-6,12-dione (5.0 g) was added gradually and stirred at room temperature for 1 hr. The reaction solution was poured into ice-cold water saturated with ammonium chloride, and unreacted starting material, dibenzimidazo-(1,2-a,1',2'-d)-tetrahydropyrazine-6,12-dione precipitated as crystals was filtered off and recovered (2.15 g). The filtrate was extracted with chloroform, washed with water and dried, and the solvent was distilled off. Recrystallization of the residue from a mixed solution of chloroform/isopropyl ether gave the title compound (2.25 g).
M.P. 201.5° C.
IR (nujol): 3340, 3220, 1635, 1570, 1405, 1105, 730 (cm$^{-1}$)
$^1$H-NMR (CDCl$_3$, TMS): 6.82 (s, 1H), 6.96 (t, 1H), 7.1–7.9 (7H), 8.09 (d, 1H), 10.82 (bs, 1H)

EXAMPLE 8

1-Methyl-N-methyl-N-(2-pyridyl)benzimidazole-2-carboxamide

N-Methyl-N-(2-pyridyl)benzimidazole-2-carboxamide (1.0 g) prepared in Example 5 was suspended in dry DMSO (20 ml), sodium hydride (0.16 g) was added in an argon atmosphere and stirred at room temperature for 1 hr. Methyl iodide (0.62 g) was added and stirred at room temperature for 2 hrs. The mixture was poured into water and extracted with chloroform. The chloroform layer was dried over anhydrous Na$_2$SO$_4$, and the solvent was distilled off to obtain the residue. Purification of the residue by column chromatography on silica gel gave the title compound (0.99 g).
IR (nujol): 1650, 1580, 1105, 745 (cm$^{-1}$)
$^1$H-NMR (CDCl$_3$, TMS): 3.66 (s, 3H), 3.98 (s, 3H), 7.05 (dd, 1H), 7.15–7.7 (6H), 8.19 (d, 1H)

EXAMPLE 9

1-Acetyl-N-methyl-N-(2-pyridyl)benzimidazole-2-carboxamide

N-Methyl-N-(2-pyridyl)benzimidazole-2-carboxamide (1.5 g) prepared in Example 5 was suspended in dry pyridine (20 ml), anhydrous acetic acid (1.5 g) was added at room temperature while stirring and allowed to react overnight. Pyridine was distilled off under reduced pressure, the residue was dissolved in ethyl acetate, washed with water and dried over anhydrous Na$_2$SO$_4$, and the solvent was distilled off. Purification of the residue by column chromatography on silica gel gave the title compound (0.75 g).
IR (nujol): 1720, 1655, 1590, 1305, 765 (cm$^{-1}$)
$^1$H-NMR (CDCl$_3$, TMS): 2.89 (s, 3H), 3.65 (s, 3H), 7.01 (t, 1H), 7.2–7.6 (4H), 7.70 (t, 1H), 7.99 (m, 1H), 8.16 (d, 1H)

EXAMPLE 10

1-(β-Dimethylaminoethyl)-N-(2-pyridyl)benzimidazole-2-carboxamide

N-(2-pyridyl)benzimidazole-2-carboxamide (2.0 g) prepared in Example 1 was dissolved in dry DMSO (25 ml), sodium hydride (0.35 g) was added and stirred at room temperature for 1 hr. Excess β-dimethylaminoethyl chloride was added to the mixture and allowed to react overnight at room temperature under agitation. The reaction solution was poured into aqueous saturated ammonium chloride solution and extracted with chloroform. The chloroform layer was dried over anhydrous Na$_2$SO$_4$ and the solvent was distilled off. Purification of the residue by column chromatography on silica gel gave the title compound (0.84 g).

IR (neat): 3350, 3050, 1680, 1580, 1300, 740 (cm$^{-1}$)
$^1$H-NMR (CDCl$_3$, TMS): 2.35 (s, 6H), 2.77, (t, 2H), 4.85 (t, 2H), 7.06 (dd, 1H), 7.25–7.85 (5H), 8.31 (d, 1H), 8.38 (dd, 1H), 10.17 (bs, 1H)

EXAMPLE 11

N-(4,6-Dimethyl-2-pyridyl)-5,6-dimethoxybenzimidazole-2-carboxamide

In a dry argon atmosphere, 2-amino-4,6-dimethyl pyridine (4.0 g) was dissolved in dry DMSO (30 ml), 60% sodium hydride (1.30 g) was added and stirred at room temperature for 1 hr. A solution of 1-(N,N-dimethylsulfamoyl)-2-ethoxycarbonyl-5,6-dimethoxybenzimidazole (6.56 g) in DMSO (15 ml) was added dropwise while cooling and stirred at room temperature for 2 hrs. The reaction solution was poured into aqueous saturated ammonium chloride solution and extracted with benzene. The residue obtained by distilling off the solvent was purified by column chromatography on silica gel to obtain N-(4,6-dimethyl-2-pyridyl)-1-(N,N-dimethylsulfamoyl)-5,6-dimethoxybenzimidazole-2-carboxamide (5.40 g). This compound was dissolved in THF (250 ml), and then water (70 ml) and conc. hydrochloric acid (7 ml) were added allowed to react overnight at room temperature under agitation. The reaction solution was neutralized with ammonia water, THF was distilled off and the precipitated crystals were filtered off. The crystals obtained was recrystallized from chloroform/methanol to give the title compound (3.45 g).

M.P. 255.6° C.
IR (nujol): 3360, 3245, 1680, 1610, 1560, 835 (cm$^{-1}$)
$^1$H-NMR (CDCl$_3$, TMS):2.36 (s, 3H), 2.46 (s, 3H), 3.91 (s, 3H), 3.98 (s, 3H), 6.80 (s, 1H), 6.95 (s, 1H), 7.25 (s, 1H), 8.00 (s, 1H), 9.75 (bs, 1H), 10.90 (bs, 1H)

EXAMPLE 12

N-(2-pyridyl)-5-methylbenzimidazole-2-carboxamide

In an argon atmosphere, 2-aminopyridine (0.85 g) was dissolved in dry dichloromethane (15 ml), and 5.1 ml of trimethylaluminum (19% n-hexane solution) were added dropwise while ice-cooling and reacted at room temperature for 1 hr. A solution of 1-(N,N-dimethylsulfamoyl)-2-ethoxycarbonyl-5(and 6)-methylbenzimidazole (2.00 g) in dichloromethane was added dropwise and reacted at room temperature for 2 days. Diluted hydrochloric acid was added dropwise while vigorously stirring and, the organic layer was separated and dried over Na$_2$SO$_4$. Purification of the residue obtained by distilling off the solvent by column chromatography on silica gel gave N-(2-pyridyl)-1-(N,N-dimethylsulfamoyl)-5(and 6)-methylbenzimidazole-2-carboxamide (0.78 g). This compound was dissolved in THF (30 ml), and water (15 ml) and conc. hydrochloric acid (2 ml) were added and reacted at room temperature for 24 hrs. The reaction solution was neutralized with ammonia water, THF was distilled off, and the precipitated crystals were filtered off and recrystallized from chloroform/methanol to give the title compound (0.27 g).

M.P. 230.0° C.
IR (KBr): 3420, 3360, 1680, 1540, 1435, 1300, 780 (cm$^{-1}$)
$^1$H-NMR (CDCl$_3$+CD$_3$OD, TMS): 2.51 (s, 3H), 7.18 (m, 2H), 7.46 (m, 1H), 7.59 (dd, 1H), 7.79 (dt, 1H), 8.27 (d, 1H), 8.89 (dd, 1H)

EXAMPLE 13

N-Methyl-N-(4,6-dimethyl-2-pyridyl)-1-[2-(4-(3,4-dimethoxybenzoyl)-1-piperazinyl)ethyl]benzimidazole-2-carboxamide In an argon atmosphere, N-methyl-N-(4,6-dimethyl-2-pyridyl)benzimidazole-2-carboxamide (2.00 g) was dissolved in DMSO (15 ml), and 60% sodium hydride (0.33 g) was added and stirred at room temperature for 1 hr. A solution (7 ml) of 2-[4-(3,4-dimethoxybenzoyl)-1-piperazinyl]ethyl chloride (2.20 g) in DMSO was added dropwise and allowed to react overnight at room temperature under agitation. The reaction solution was added to an aqueous solution of ammonium chloride and extracted with chloroform, the chloroform layer was dried over Na$_2$SO$_4$, and the solvent was distilled off. Purification of the residue by column chromatography gave the title compound (3.10 g) as amorphous solid.

IR (KBr): 1630, 1610, 1515, 1480, 1430, 1260, 750 (cm$^{-1}$)
$^1$H-NMR (CDCl$_3$, TMS); 2.18 (s, 3H), 2.24 (s, 3H), 2.4–2.65 (8H), 2.89 (t, 2H), 3.64 (s, 3H), 3.89 (s, 3H), 3.90 (s, 3H), 4.59 (t, 2H), 6.71 (s, 1H), 6.8–7.05 (4H), 7.15–7.45 (3H), 7.61 (d, 1H)

EXAMPLE 14

N-(2-Pyridyl)-1-[2-(4-(2-methoxyphenyl)-1-piperazinyl)ethyl]benzimidazole-2-carboxamide In an argon atmosphere, N-(2-pyridyl)benzimidazole-2-carboxamide (1.55 g) was dissolved in DMSO (20 ml), and 60% sodium hydride (0.28 g) was added and stirred at room temperature for 1 hr. A solution (7 ml) of 2-[4-(2-methoxyphenyl)-1-piperazinyl]ethyl chloride (1.65 g) in DMSO was added dropwise and stirred at room temperature overnight. The reaction solution was poured into an aqueous solution of ammonium chloride and extracted with chloroform, and the chloroform layer was dired. The residue obtained by distilling off the solvent was purified by column chromatography on silica gel to give the title compound (1.54 g) as amorphous solid.

IR (KBr): 3350, 2810, 1695, 1525, 1435, 1300, 1240, 745 (cm$^{-1}$)
$^1$H-NMR (CDCl$_3$, TMS): 2.65–2.85 (4H), 2.88 (t, 2H), 2.95–3.10 (4H), 3.84 (s, 3H), 4.92 (t, 2H), 6.75–7.12 (5H), 7.35–7.57 (3H), 7.69–7.89 (2H), 8.32 (d, 1H), 8.37 (dd, 1H), 10.20 (bs, 1H)

EXAMPLE 15

N-(2-Pyridyl)-1-[2-(4-(3,4-dimethoxybenzoyl)-1-piperazinyl)ethyl]-5,6-dimethoxybenzimidazole-2-carboxamide In an argon atmosphere, N-(2-pyridyl)-5,6-dimethoxybenzimidazole-2-carboxamide (0.85 g) was dissolved in DMSO (15 ml), and 60% sodium hydride (0.16 g) was added and stirred at room temperature for 1 hr. A solution (5 ml) of 2-[4-(3,4-dimethoxybenzoyl)-1-piperazinyl]ethyl chloride (1.25 g) in DMSO was added dropwise and allowed to react overnight at room temperature under agitation. After-treatment and purification in the same manner as described in Example 14 gave the title compound (0.72 g) as amorphous solid.

IR (KBr): 3360, 1695, 1630, 1525, 1440, 1220, 1140, 1015 (cm$^{-1}$)

¹H-NMR (CDCl₃, TMS): 2.40-2.65 (4H), 2.84 (t, 2H), 3.35-3.65 (4H), 3.87 (s, 3H), 3.88 (s, 3H), 3.99 (s, 3H), 4.00 (s, 3H), 4.85 (t, 2H), 6.75-6.98 (4H), 7.07 (dd, 1H), 7.21 (s, 1H), 7.75 (t, 1H), 8.28 (d, 1H), 8.38 (dd, 1H), 10.05 (bs, 1H)

EXAMPLE 16

N-(2-pyridyl)-1-[2-(4-(3,4-dimethoxybenzoyl)-1-piperazinyl)ethyl]benzimidazole-2-carboxamide In an argon atmosphere, N-(2-pyridyl)benzimidazole-2-carboxamide (1.40 g) was dissolved in DMSO (20 ml), and 60% sodium hydride (0.28 g) was added and stirred at room temperature for 1 hr. A solution (7 ml) of 2-[4-(3,4-dimethoxybenzoyl)-1-piperazinyl]ethyl chloride (1.90 g) in DMSO was added dropwise and allowed to react overnight at room temperature under agitation. The reaction solution was poured into an aqueous solution of ammonium chloride and extracted with chloroform. The chloroform layer was dried over Na₂SO₄ and the solvent was distilled off. Purification of the residue by column chromatography on silica gel gave the title compound (1.60 g) as amorphous solid.

IR (KBr): 3350, 1690, 1630, 1520, 1430, 1300, 745 (cm⁻¹)

¹H-NMR (CDCl₃, TMS): 2.55 (m, 4H), 2.83 (t, 2H), 3.52 (m, 4H), 3.88 (s, 3H), 3.90 (s, 3H), 4.90 (t, 2H), 6.75-6.95 (m, 3H), 7.10 (dd, 1H), 7.30-7.55 (m, 3H), 7.70-7.89 (m, 2H), 8.28 (d, 1H), 8.39 (dd, 1H), 10.15 (bs, 1H)

EXAMPLE 17

N-Methyl-N-(2-pyridyl)-1-[2-(4-(3,4-dimethoxybenzoyl)-1-piperazinyl)ethyl]benzimidazole-2-carboxamide N-Methyl-N-(2-pyridyl)benzimidazole-2-carboxamide (1.70 g) was reacted and after-treated in the same manner as described in Example 16 to give the title compound (1.98 g) as amorphous solid.

IR (KBr): 3430, 1650, 1630, 1460, 1435, 1263, 745 (cm⁻¹)

¹H-NMR (CDCl₃, TMS): 2.55 (m, 4H), 2.86 (t, 2H), 3.58 (m, 4H), 3.70 (s, 3H), 3.89 (s, 3H), 3.90 (s, 3H), 4.62 (t, 2H), 6.78-6.98 (m, 3H), 7.06 (dd, 1H), 7.15-7.45 (m, 4H), 7.53-7.65 (m, 2H), 8.29 (dd, 1H)

EXAMPLES 18-55

The compounds shown in Tables 1 and 2 were prepared by using the appropriate starting materials and the procedures described in Examples 1-17. In the tables, NMR data were determined in CDCl₃ on the basis of TMS unless otherwise specified.

TABLE 1

Structure: benzimidazole core with R¹ substituent, N-R³, C(=O)-N(R²)-pyridine with R⁴ substituent

| Example | R¹ | R² | R³ | R⁴ | Property | IR | ¹H-NMR |
|---|---|---|---|---|---|---|---|
| 18 | H | piperidine-N-C(=O)-phenyl(3-OMe, 4-OMe), N-butyl | H | 4,6-di Me | amorphous solid | 3350, 1690, 1630, 1530, 1425, 1263, 745(KBr) | 2.36(s,3H), 2.46(s,3H), 2.35~2.7(4H), 2.82(t,2H), 3.3~3.7(4H), 3.86(s,3H), 3.87(s,3H), 4.90(t,2H), 6.75~7.0(4H), 7.3~7.5(3H), 7.81(m,1H), 7.93(s,1H), 10.05(s,1H) |
| 19 | MeO | " | H | 4,6-di Me | amorphous solid | 3360, 1695, 1630, 1530, 1430, 1220, 1140, 1015, 750(KBr) | 2.35(s,3H), 2.44(s,3H), 2.4~2.6(4H), 2.82(t,2H), 3.4~3.65(4H), 3.89(s,3H), 3.90(s,3H), 3.97(s,3H), 3.99(s,3H), 4.82(t,2H), 6.7~7.0(tH), 7.21(s,1H) |
| 20 | H | piperidine-N-C(=O)-furyl, N-butyl | Me | 4,6-di Me | amorphous solid | 3420, 1650, 1610, 1430, 1350, 1185, 750(KBr) | 2.18(s,3H), 2.24(s,3H), 2.60(t,4H), 2.88(t,2H), 3.66(s,3H), 3.78(m,4H), 4.60(t,2H), 6.46(dd,1H), 6.71(s,1H), 6.98(d,1H), 6.99(s,1H), 7.2~7.47(4H), 7.62(d,1H) |
| 21 | H | piperazine-N-CH₂φ, N-butyl | Me | 4,6-di Me | oily product | 2830, 1660, 1615, 1460, 1355, 1070, 750(neat) | 2.19(s,3H), 2.20(s,3H), 2.35~2.55(4H), 2.85(t,2H), 3.50(s,2H), 2.63(s,3H), 4.57(t,2H), 6.70(s,1H), 6.98(s,1H), 7.15~7.45(8H), 7.59(d,1H) |
| 22 | H | piperidine-N-phenyl(2-OEt), N-butyl | Me | 4,6-di Me | amorphous solid | 3420, 1660, 1500, 1450, 1240, 745(KBr) | 1.45(t,3H), 2.18(s,6H), 2.75(4H), 2.91(t,2H), 3.09(4H), 3.67(s,3H), 4.05(q,2H), 4.63(t,2H), 6.70(s,1H), 6.75~7.05(5H), 7.15~7.5(3H), 7.62(d,1H) |
| 23 | H | N-butyl-φ | H | 4-Me | amorphous solid | 3360, 1690, 1460, 1240, 745(KBr) | 2.41(s,3H), 2.7~2.82(4H), 2.89(t,2H), 2.95~3.1(4H), 3.87(s,3H), 4.92(t,2H), 6.75~7.05(5H), 7.3~7.55(3H), 7.82(m,1H), 8.16(s,1H), 8.22(d,1H), 10.12(s,1H) |
| 24 | H | " | H | 4,6-di Me | amorphous solid | 3350, 1690, 1610, 1530, 1460, 1240, 740(KBr) | 2.37(s,3H), 2.95(s,3H), 2.65~2.8(4H), 2.89(t,2H), 2.95~3.1(4H), 3.85(s,3H), 4.91(t,2H), 6.75~7.05(5H), 7.3~7.55(3H), 7.81(m,1H), 7.96(s,1H), 10.05(bs,1H) |
| 25 | H | N-ethyl-φ | Me | 4,6-di Me | 140.8° C. | 1645, 1610, 750(nujol) | 2.16(s,3H), 2.21(s,3H), 3.58(s,3H), 5.65(s,2H), 6.70(s,1H), 6.72(s,1H), 7.1~7.45(8H), 7.38(m,1H) |

TABLE 1-continued

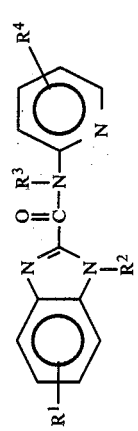

| Example | R¹ | R² | R³ | R⁴ | Property | IR | ¹H—NMR |
|---|---|---|---|---|---|---|---|
| 26 | H | " | H | 4,6-di Me | 170° C. | 3350, 1685, 1530, 1450, 1225, 750, 700(KBr) | 2.34(s,3H), 2.46(s,3H), 6.05(s,2H), 6.78(s,1H), 7.24~7.39(m,8H), 7.84(t,1H), 7.95(s,1H), 10.14(s,1H) |
| 27 | H | 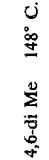 | H | 4,6-di Me | 148° C. | 3360, 1690, 1545, 1470, 1230, 755, 745, 705(KBr) | 2.39(s,3H), 2.47(s,3H), 3.20(d,2H), 4.95(d,2H), 6.80(s,1H), 7.81(d,1H), 7.97(s,1H), 10.05(s,1H), 7.12~7.37(m,8H) |
| 28 | H | 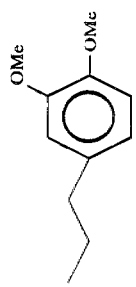 | H | 4,6-di Me | 129.5° C. | 3355, 1690, 1540, 1470, 1260, 1230, 1030,750(KBr) | 2.38(s,3H), 2.46(s,3H), 3.13(t,2H), 3.73(s,3H), 3.79(s,3H), 4.94(t,2H), 6.50(d,1H), 6.69(d,1H), 6.71(s,1H), 6.80(s,1H), 7.25~7.35(m,3H), 7.78~7.82(m,1H), 7.94(s,1H), 10.01(s,1H) |
| 29 | H | COOH | H | 4,6-di Me | 232.4° C. | 1690, 1550, 1460, 1230, 745(KBr) | (DMSO-d₆) 2.33(s,3H), 2.40(s,3H), 5.48(s,2H), 6.92(s,1H), 7.35~7.50(m,2H), 7.75~7.86(m,4H), 10.00(s,1H) |
| 30 | Me O | 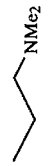NMe₂ | H | 4,6-di Me | 135.2° C. | 3380, 1700, 1620 1540, 1210, 1015 (nujol) | 2.36(s,9H), 2.45(s,3H), 2.77(t,2H), 3.98(s,3H), 4.00(s,3H), 4.80(t,2H), 6.76(s,1H), 6.86(s,1H), 7.19(s,1H), 7.95(s,1H), 9.96(bs,1H) |
| 31 | H | " | Me | 4,6-di Me | 93.5° C. | 1640, 1610, 1510, 750(nujol) | 2.21(s,6H), 2.32(s,6H), 2.80(t,2H), 3.63(s,3H), 4.54(t,2H), 6.70(s,1H), 7.01(s,1H), 7.15~7.45(3H), 7.60(d,1H) |
| 32 | H | " | H | 4,6-di Me | 123.6° C. | 3340, 2750, 1680, 1610, 1530, 1460, 1430, 1220, 750(KBr) | 2.38(s,9H), 2.49(s,3H), 2.79(t,2H), 4.87(t,2H), 6.79(s,1H), 7.34~7.55(m,3H), 7.82(d,1H), 7.98(s,1H), 10.09(s,1H) |
| 33 | H | " | H | 5-Me | 102.1° C. | 3350, 1675, 1520 1460, 1310, 735(KBr) | 2.35(s,3H), 2.38(s,6H), 2.79(t,2H), 4.88(t,2H), 7.30~7.60(m,4H), 7.81(d,1H), 8.20(s,1H), 8.22(d,1H), 10.11(s,1H) |
| 34 | H | Me | H | H | crystal | 3350, 1700, 1580, 1540, 1445, 1315, 900, 745(nujol) | 4.24(s,3H), 7.10(dd,1H), 7.3~7.5(3H), 7.7~7.9(2H), 8.30(d,1H), 8.38(dd,1H), 10.15(bs,1H) |
| 35 | Me O | H | H | H | 259.5° C. | 3350, 3260, 1675, 1550, 1305, 1225 (nujol) | 3.97(s,3H), 3.98(s,3H), 6.99(s,1H), 7.10(dd,1H), 7.25(1H), 7.77(dt,1H), 8.35(dd,1H), 8.38(dd,1H), 9.70(bs,1H), 10.55(bs,1H) |
| 36 | H | H | H | 3-Me | 236° C. | 3350, 1670, 1530 1445, 1230, 870, 740(nujol) | (CDCl₃/CD₃ OD = 5/1) 2.43(s,3H), 7.20(dd,1H), 7.38(2H), 7.61(m,1H), 7.66(d,1H), 7.81(m,1H), 8.35(dd,1H) |

TABLE 1-continued

[Structure: benzimidazole with R¹ on benzene ring, R² on N, and C(=O)-N(R³)-pyridyl(R⁴) substituent]

| Example | R¹ | R² | R³ | R⁴ | Property | IR | ¹H—NMR |
|---|---|---|---|---|---|---|---|
| 37 | H | H | H | 5-Me | 205.8° C. | 3400, 1690, 1640 1500, 1410, 1315, 1235, 1140, 840, 755, 745(KBr) | 2.36(s,3H), 7.30~7.45(m,2H), 7.50~7.65(m,2H), 7.85(d,1H), 8.27(2H), 9.98(s,1H), 11.23(s,1H) |
| 38 | H | H | H | 6-Me | 238.0° C. | 3350, 3230, 1660, 1540, 1220, 785, 745(nujol) | (CDCl₃/CD₃OD = 5/1) 2.5(s,3H), 6.98(d,1H), 7.35(m,2H), 7.56(m,1H), 7.66(t,1H), 7.85(m,1H), 8.10(d,1H) |
| 39 | H | H | H | 4,6-di Me | 265.6° C. | 1710, 1630, 1600, 1310, 1280, 1240, 770(KBr) | 2.39(s,3H), 2.47(s,3H), 6.82(s,1H), 7.28~7.45(m,2H), 7.58~7.62(m,1H), 7.85(dd,1H), 8.01(s,1H), 9.84(br,1H), 10.73(br,1H) |
| 40 | H | H | H | 4-φ | 238.3° C. | 3350, 3250, 1675, 1540, 1410, 1315, 1210, 750(KBr) | (DMSO—d₆) 7.30~7.45(m,2H), 7.50~7.65(m,6H), 7.65~7.85(m,3H), 8.49(2H), 10.20(br,1H) |
| 41 | H | H | H | 5-NO₂ | crystal | 3270, 1670, 1605, 1530, 1350, 1290, 1215, 1115, 750(KBr) | (DMSO—d₆) 7.37(m,2H), 7.40(d,1H), 7.81(d,1H), 8.41(d,1H), 8.71(d,1H), 9.22(s,1H), 10.80(s,1H), 1372(s,1H) |
| 42 | H | H | Me | 4,6-di Me | 155.9° C. | 3300, 1680, 1620, 1335, 1080, 750 (nujol) | 2.30(s,3H), 2.44(s,3H), 3.86(s,3H), 6.91(s,1H), 7.02(s,1H), 7.15~7.45(3H), 7.69(d,1H), 11.05(bs,1H) |

TABLE 2

$$\underset{R^1}{\text{[benzimidazole]}}-\underset{R^2}{\overset{R^3}{\underset{|}{C}}}\overset{O}{\underset{\|}{-}}\text{N-Het}$$

| Example | R¹ | R² | R³ | Het | M.P. | IR | ¹H—NMR |
|---|---|---|---|---|---|---|---|
| 43 | H | H | H | 4-pyridyl | 200° C. (dec.) | 3150, 3050, 1690, 1595, 1550, 1330, 1130, 805(nujol) | (CDCl₃/CD₃OD=5/1)7.35~7.5(3H), 7.62(1H), 7.80(1H), 8.29(m,1H), 8.37(m,1H), 8.99(d,1H) |
| 44 | H | H | H | 4-pyridyl | 287° C. | 3300, 1700, 1595, 1510, 1330, 1210, 1010, 735 (nujol) | (DMSO—d₆)7.36(m,2H), 7.60(d,1H), 7.82(d,1H), 7.97(d,2H), 8.51(d,2H) |
| 45 | H | H | H | pyrazinyl | 277° C. (dec.) | 3350, 3250, 1680, 1540, 1415, 1305, 1015, 840 (nujol) | (DMSO—d₆)7.35(m,2H), 7.71(m,2H), 8.50(m,2H), 9.41(d,1H) |
| 46 | H | H | H | pyrimidinyl | 271° C. | 3350, 1705, 1575, 1520, 1440, 1310, 1200, 750 (nujol) | (DMSO—d₆)7.15(dt,2H), 7.16(2H), 7.78(1H), 7.89(1H), 8.38(d,1H), 10.22(bs,1H), 12.80(bs,1H) |
| 47 | H | H | H | imidazolyl | >300° C. | 3350, 1660, 1610, 1540, 1040, 890, 725(nujol) | (DMSO—d₆)7.70(2H), 7.60(1H), 7.75(1H), 8.22(1H), 12.0(1H), 13.55(2H) |
| 48 | H | H | H | 2-methylquinolinyl | 276.8° C. | 3250, 3200, 3010, 1670, 1590, 1530, 1495, 1420, 1320, 1220, 910, 820, 730(KBr) | (DMSO—d₆)7.39(m,2H), 7.53~7.64(m,2H), 7.72~8.01(m,4H), 8.47((dd)2H), 10.39(s,1H), 13.70(br,1H) |

TABLE 2-continued

![structure: benzimidazole with R1 on benzene ring, R2 on N, C(=O)N(R3)-Het substituent]

| Example | R¹ | R² | R³ | Het | M.P. | IR | ¹H—NMR |
|---|---|---|---|---|---|---|---|
| 49 | H | H | H | naphthalen-1-yl | 113.2° C. | 3400, 3180, 1585, 1530, 1340, 1330, 750(KBr) | 7.25~8.00(m,8H), 8.10(s,1H), 8.45(s,1H), 10.40(br,1H), 11.70(br,1H) |
| 50 | MeO | H | H | 4-methylpyridin-3-yl | 295.0° C. | 3440, 3360, 1695, 1580, 1530, 1510, 1260, 1195, 1000 (nujol) | (CDCl₃/CD₃OD=5/1)3.99(s,6H), 7.08(2H), 7.75(d,2H), 8.52(d,2H) |
| 51 | MeO | H | H | 2-OMe-pyridazinyl | 289° C. ( ) | 3370, 3240, 1675, 1550, 1305, 1245, 1015, 840 (nujol) | (CDCl₃/CD₃OD=5/1)3.97(s,6H), 4.12(s,3H), 7.01(s,1H), 7.11(d,1H), 7.24(s,1H), 8.49(d,1H) |
| 52 | H | CH₂CO₂Et | H | 6-methylpyridin-3-yl | 128.8° C. | 3310, 1750, 1670, 1555, 1465, 1210, 1200, 750(KBr) | 1.25(t,3H), 4.25(q,2H), 4.76(d,2H), 5.40(s,2H), 7.15~7.46(m,5H), 7.66(t,1H), 7.85(d,1H), 8.61(br,2H) |
| 53 | H | CH₂CO₂Et | H | 2,6-dimethylpyridin-4-yl | 168.2° C. | 1735, 1680, 1530, 1450, 1210, 740 | 1.27(t,3H), 2.35(s,3H), 2.46(s,3H), 4.25(q,2H), 5.50(s,2H), 6.79(s,1H), 7.30~7.47(m,3H), 7.83~7.87(m,1H), 7.92(s,1H), 10.04(s,1H) |
| 54 | H | CH₂CO₂Et | H | 6-phenylpyridin-3-yl | 187.2° C. | 3310, 1730, 1685, 1540, 1520, 1405, 1210, 755, 730 | 1.28(t,3H), 4.24(q,2H), 5.51(s,2H), 7.25~7.52(m,8H), 7.65~7.75(m,2H), 7.85~7.91(m,1H), 8.40(d,1H), 8.55(s,1H), 10.21(s,1H) |

TABLE 2-continued

| Example | R¹ | R² | R³ | Het | M.P. | IR | ¹H—NMR |
|---|---|---|---|---|---|---|---|
| 55 | | | ![structure] | ![structure] | 186.2° C. | 3050, 1735, 1530, 1315, 1210, 1020, 750(nujol) | (CDCl₃/CD₃OD=5/1)4.05(s,2H), 7.38(m,4H), 7.67(4H) |

The cardiotonic activity of the compounds of the present invention was evaluated by the following method.

METHOD

Right and left atria of guinea-pigs suspended in Magnus bath containing Krebs-Henseleit solution which was maintained at 33° C. A mixed gas consisting of 95% $O_2$ and 5% $CO_2$ was bubbled through the solution. The atrial muscle was loaded with the tension of 0.5 g, attached to a strain gauge, and the contractility of left atrium caused by electric stimulation and the rate of right atrium were recorded.

The activities of the test compounds in a concentration of $1 \times 10^{-4}$ M are shown in Table 3.

The results are expressed as per cent (%) changes of contractility in atrium muscle and rate which are calculated according to the following equation.

Change of Contractility (%):

$$\frac{\text{(Contractility after addition)} - \text{(Contractility before addition)}}{\text{Contractility before addition}} \times 100$$

Change of Rate (%):

$$\frac{\text{(Rate after addition)} - \text{(Rate before addition)}}{\text{Rate before addition}} \times 100$$

TABLE 3

| Test compound | Percent Change Cardiac Contractility | Rate |
|---|---|---|
| Example 1 | 600.9 | 3.1 |
| 2 | 71.0 | −5.4 |
| 3 | 79.9 | 26.8 |
| 4 | 52.5 | −4.4 |
| 6 | 91.5 | −10.9 |
| 7 | 178.6 | −7.5 |
| 10 | 45.8 | −40.5 |
| 12 | 96.9 | −0.3 |
| 13 | 121.8 | −41.0 |
| 15 | 39.3 | −26.8 |
| 16 | 49.8 | −32.5 |
| 17 | 104.9 | −25.8 |
| 20 | 71.0 | −26.6 |
| 37 | 105.4 | −10.4 |
| 48 | 63.2 | −6.3 |
| 54 | 36.9 | −2.8 |
| Dopamine hydrochloride (Control) | 202.5 | 81.9 |

Acute Toxicity in mice

The acute toxicity of the compound (Example 1) of the invention was investigated using mice. The test compound was administered intravenously. $LD_{50}$ (i.v.) was more than 750 mg/kg. Thus, the acute toxicity of the present compound was found to be very low as compared with 190 mg/kg of dopamine hydrochloride as a control compound.

The following examples illustrate how the compounds of the invention can be incorporated in pharmaceutical preparations.

| Example 56 Tablets | |
|---|---|
| Each tablet contains | |
| N—(2 pyridyl)benzimidazole-2-carboxamide (active ingredient) | 10 mg |
| Lactose | 67 mg |
| Crystalline cellulose | 15 mg |
| Cornstarch | 7 mg |
| Magnesium stearate | 1 mg |
| | 100 mg |

The above components were mixed uniformly to prepare the powders for direct compressing. These powders were molded by means of a rotary tablet machine to tablets, each having 6.3 mm diameter and each weighing 100 mg.

| Example 57 Granules | |
|---|---|
| Each package contains | |
| A | |
| N—(2-Pyridyl)benzimidazole-2-carboxamide (active ingredient) | 10 mg |
| Lactose | 90 mg |
| Cornstarch | 50 mg |
| Crystalline cellulose | 50 mg |
| B | |
| Hydroxypropyl cellulose | 10 mg |
| Ethanol | 90 mg |

The components A were mixed uniformly and the solutions B were added. The mixture was kneaded together, granulated by an extrusion granulating method, and dried by a dryer at 50° C. The dried granulate was passed through a mesh screen to classify into the particle sizes ranging from 297 μm to 1460 μm for the granule preparations, each package weighing 200 mg.

| Example 58 Syrup | |
|---|---|
| N—(2-Pyridyl)benzimidazole-2-carboxamide (active ingredient) | 1,000 g |
| White sugar | 30,000 g |
| D-sorbitol 70 w/v % | 25,000 g |
| Ethyl p-hydroxybenzoate | 0.030 g |
| Propyl p-hydroxybenzoate | 0.015 g |
| Flavoring agent | 0.200 g |
| Glycerin | 0.150 g |
| 96% Ethanol | 0.500 g |
| Distilled water | ad 100 ml |

White sugar, D-sorbitol, ethyl p-hydroxybenzoate, propyl p-hydroxybenzoate and the active ingredient were dissolved in 60 g of hot water. After cooling the mixture, there was added a solution of a flavoring agent dissolved in glycerin and ethanol. Water was added to make 100 ml.

| Example 59 Injection Solution | |
|---|---|
| N—(2-Pyridyl)benzimidazole-2-carboxamide (active ingredient) | 1 mg |
| Sodium chloride | 10 mg |
| Distilled water | ad 1.0 ml |

Sodium chloride and the active ingredient were added to distilled water to make 1.0 ml.

| Example 60 Suppositories | |
|---|---|
| N—(2-Pyridyl)benzimidazole-2-carboxamide (active ingredient) | 2 g |
| Polyethylene glycol 4000 | 20 g |
| Glycerin | 78 g |
| Total | 100 g |

Glycerin was added to the active ingredient and dissolved. Polyethylene glycol 4000 was added to the solution, warmed and poured into a mold for suppository. The content was cooled for solidification to prepare suppositories each weighing 1.5 g.

What is claimed is:

1. A compound of Formula I

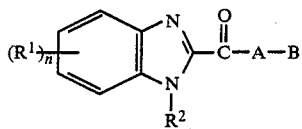

wherein $R^1$ is a hydrogen atom, a $(C_1-C_3)$ alkyl group, a $(C_1-C_3)$ alkoxy group or a halogen atom;
n is 1 to 4;
$R^2$ is a hydrogen atom, a $(C_1-C_4)$ alkyl group, an amino $(C_2-C_3)$ alkyl group, a mono- or di- $(C_1-C_3)$ alkyl-amino $(C_2-C_3)$ alkyl group, acetyl, propionyl, butyryl, stearoyl, benzyl, phenethyl, a carboxy $(C_1-C_3)$ alkyl group, a $(C_1-C_3)$ alkoxy carbonyl $(C_1-C_3)$ alkyl group or $(C_2-C_4)$

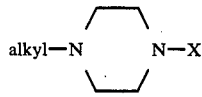

wherein X is a $(C_1-C_3)$ alkoxy phenyl group benzyl, a $(C_1-C_3)$ alkoxybenzoyl or furoyl group;
A is —$NR^3$— where $R^3$ is hydrogen or $(C_1-C_3)$ alkyl, a $(C_1-C_4)$ alkylene or a $(C_2-C_4)$ alkyldiene; and
B is a heterocylic group selected from triazolyl, pyridyl, pyridazinyl pyrimidinyl, pyrazinyl, benzimidozolyl, benzothiazolyl, quinolyl and isoquinolyl, said heterocyclic group being optionally substituted by one or more $(C_1-C_3)$ alkyl, $(C_1-C_3)$ alkoxy, nitro or phenyl groups, or the physiologically acceptable acid addition salts thereof.

2. A compound of claim 1 wherein $R^1$ is hydrogen, $(C_1-C_3)$ alkyl or $(C_1-C_3)$ alkoxy and n is 1 or 2.

3. A compound of claim 1 wherein $R^2$ is hydrogen, $(C_1-C_4)$ alkyl di-$(C_1-C_3)$ alkylamino $(C_2-C_3)$ alkyl, acetyl, benzyl, phenethyl, carboxy $(C_1-C_3)$ alkyl, $(C_1-C_3)$ alkoxylcarbonyl $(C_1-C_3)$ alkyl or (4-substituted -1- piperazinyl) $(C_2-C_4)$ alkyl.

4. A compound of claim 1 wherein $R^2$ is methyl, ethyl, propyl, butyl, acetyl, propionyl, butyryl, stearoyl, aminoethyl, aminopropyl, monomethylaminoethyl, dimethylaminoethyl, carboxymethyl, 3-carboxypropyl, methoxycarbonylmethyl, ethoxycarbonylmethyl, benzyl, phenethyl, (4-(dimethoxybenzoyl)-1-piperazinyl)ethyl, (4-furoyl-1-piperazinyl)ethyl, (4-benzyl-1-piperazinyl)ethyl, (4-(methoxyphenyl)-1-piperazinyl)ethyl or (4-(ethoxyphenyl)-1-piperazinyl)ethyl.

5. A compound of claim 1 wherein A is —NH—, —$N(CH_3)$—, —$N(C_2H_5)$—, methylene, ethylene, propylene, butylene, ethylidene, propylidene or butylidene.

6. A compound of claim 1 wherein B is 5-(1,2,3-triazolyl), 3-(1,2,4-triazolyl), 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-benzimidazolyl, 2-benzothiazolyl, 3-benzoisothiazolyl, 2-quinolyl or 1-isoquinolyl.

7. A compound of claim 1 wherein B is $(C_1-C_3)$ alkyl-substituted pyridyl, $(C_1-C_3)$ alkyl-substituted pyrimidinyl, phenyl-substituted pyridyl, nitro-substituted pyridyl or $(C_1-C_3)$ alkoxy-substituted benzothiazolyl.

8. A pharmaceutical composition which comprises as an active ingredient an effective amount of a compound of claim 1 or the physiologically acceptable acid addition salt thereof, optionally in admixture with additives for pharmaceutical preparations.

9. A pharmaceutical composition of claim 8 wherein the active ingredient is the compound of claim 2 or the acid addition salt thereof.

10. A pharmaceutical composition of claim 8 wherein the active ingredient is the compound of claim 3 or the acid addition salt thereof.

11. A pharmaceutical composition of claim 8 wherein the active ingredient is the compound of claim 4 or the acid addition salt thereof.

12. A pharmaceutical composition of claim 8 wherein the active ingredient is the compound of claim 5 or the acid addition salt thereof.

13. A pharmaceutical composition of claim 8 wherein the active ingredient is the compound of claim 6 or the acid addition salt thereof.

14. A pharmaceutical composition of claim 8 wherein the active ingredient is the compound of claim 7 or the acid addition salt thereof.

* * * * *